(12) United States Patent
Turner et al.

(10) Patent No.: US 7,621,946 B2
(45) Date of Patent: Nov. 24, 2009

(54) IMPLANTABLE MEDICAL ENDOPROSTHESIS DELIVERY SYSTEM WITH HUB

(75) Inventors: Karen Turner, Lino Lakes, MN (US); John Blix, Maple Grove, MN (US); John R. Moberg, Elk River, MN (US); Michael Gerdts, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 649 days.

(21) Appl. No.: 11/368,876

(22) Filed: Mar. 6, 2006

(65) Prior Publication Data

US 2007/0208351 A1   Sep. 6, 2007

(51) Int. Cl.
*A61F 2/06* (2006.01)
(52) U.S. Cl. .................................... 623/1.11
(58) Field of Classification Search ............... 623/1.11; 606/108; 600/435, 156; 137/561 R; 138/40; 604/523, 533, 534, 535, 96.01, 99.02, 99.03, 604/99.04, 249
See application file for complete search history.

(56) References Cited

U.S. PATENT DOCUMENTS

| | | | |
|---|---|---|---|
| 4,886,507 A | 12/1989 | Patton et al. | |
| 5,195,980 A | 3/1993 | Catlin | |
| 5,228,452 A | 7/1993 | Samson | |
| 5,269,764 A | 12/1993 | Vetter et al. | |
| 5,478,331 A | 12/1995 | Heflin et al. | |
| 5,733,267 A | 3/1998 | Del Toro | |
| 5,823,961 A * | 10/1998 | Fields et al. | 600/434 |
| 5,993,416 A * | 11/1999 | Choh et al. | 604/99.02 |
| 6,217,586 B1 | 4/2001 | Mackenzie | |
| 6,695,820 B1 | 2/2004 | Armstrong et al. | |
| 6,786,918 B1 * | 9/2004 | Krivoruchko et al. | 623/1.11 |
| 6,945,969 B1 | 9/2005 | Morris et al. | |
| 2002/0095203 A1 | 7/2002 | Thompson et al. | |
| 2002/0165523 A1 | 11/2002 | Chin et al. | |
| 2003/0074045 A1 | 4/2003 | Buzzard et al. | |
| 2004/0062891 A1 | 4/2004 | Horn et al. | |

(Continued)

FOREIGN PATENT DOCUMENTS

EP    1 181 905    2/2002

(Continued)

OTHER PUBLICATIONS

International Search Report and Written Opinion; PCT/US2007/062877; mailed Dec. 14, 2007.

*Primary Examiner*—Todd E Manahan
*Assistant Examiner*—Leander Taylor, III
(74) *Attorney, Agent, or Firm*—Crompton, Seager & Tufte, LLC

(57) ABSTRACT

Implantable medical endoprosthesis delivery systems and methods for making and using the same. An example implantable medical endoprosthesis delivery system may include an inner member having a first lumen disposed therein. An outer member may at least partially surround the inner member so that a second lumen is disposed between the inner and outer members. The second lumen may be configured so that an implantable medical endoprosthesis can be disposed therein. The delivery system may also include a hub including a fluid introduction port, a first fluid flow path in fluid communication with the fluid introduction port, and a second fluid flow path in fluid communication with the fluid introduction port.

20 Claims, 8 Drawing Sheets

U.S. PATENT DOCUMENTS

| | | |
|---|---|---|
| 2004/0146670 A1 | 7/2004 | Chin et al. |
| 2004/0230284 A1 | 11/2004 | Headley et al. |
| 2005/0054988 A1 | 3/2005 | Rosenberg et al. |
| 2005/0245887 A1 | 11/2005 | Olsen et al. |

FOREIGN PATENT DOCUMENTS

| | | |
|---|---|---|
| EP | 1181905 | 2/2002 |
| WO | WO 02/091951 | 11/2002 |

* cited by examiner

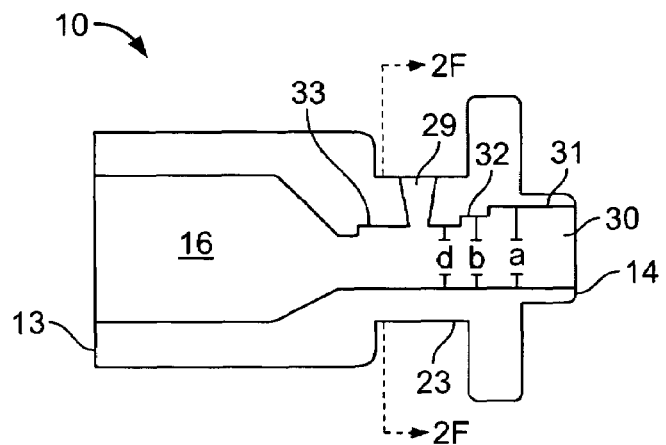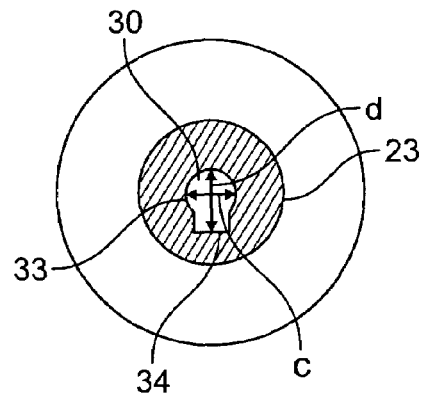
FIG. 2E    FIG. 2F
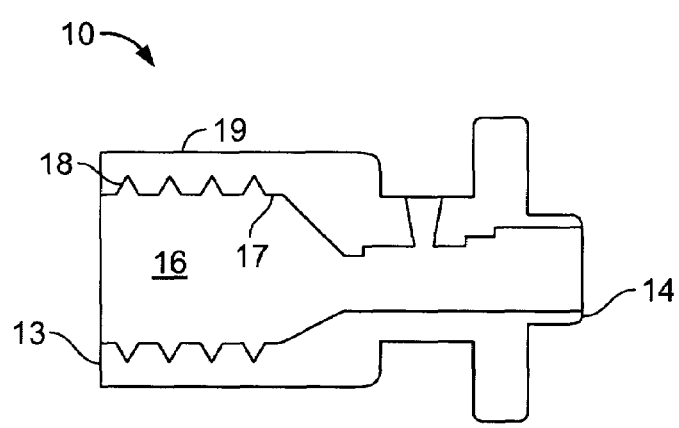
FIG. 3A

US 7,621,946 B2

IMPLANTABLE MEDICAL ENDOPROSTHESIS DELIVERY SYSTEM WITH HUB

TECHNICAL FIELD

This invention relates to endoprosthesis delivery systems.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the outer member to allow the stent to engage the occlusion/lumen wall. Thereafter, the operator removes the distal portion of the system from the lumen.

SUMMARY

In general, the hubs provided herein are adapted to receive a multi-shaft implantable medical endoprosthesis delivery system. An example of such a system is a system having an inner member and an outer member surrounding at least a portion of the inner member, where the inner member has a lumen that passes therethrough, and a second lumen is positioned between the inner member and the outer member. The hubs are designed to allow for fluid (e.g., flushing fluid) to be introduced into the hub, through which it then flows (e.g., simultaneously flows) into the lumen in an inner member and also into the lumen between the inner and outer members. In some embodiments, this is accomplished by splitting the fluid flow path into two or more channels, with at least one channel being directed into the inner member lumen and at least one channel being directed into the lumen between the inner member and the outer member.

In some embodiments, the implantable medical endoprosthesis delivery system has one lumen that is larger in transverse cross-sectional area than the one or more other lumens. To reduce the tendency for the majority of the fluid to flow into the lumen with the larger transverse cross-sectional area, a flow restrictor (e.g., a rod, pin, tube, or other elongate structure having a maximum transverse cross-sectional dimension, for example, diameter, smaller than the inner diameter of the largest lumen) can be inserted into a proximal end of the lumen. The flow restrictor can at least partially balance out the cross-sectional area through which the fluid flows (e.g., by making the transverse cross-sectional area of the largest lumen closer to that of the other lumen(s) at the proximal end of the lumens) such that a more even flow of fluid through the lumens is achieved. This can help avoid the need for multiple flushing steps.

Embodiments may include one or more of the following advantages.

In certain embodiments, the systems allow for adequate flushing of multiple (e.g., two) lumens. In some embodiments the lumens can be flushed simultaneously, using, for example, a single flush fluid source. For example, the first and second lumens can be flushed using a single syringe-full of flushing fluid (e.g., a single 10 ml syringe-full of flushing fluid). In some embodiments, the first and second lumens can be flushed using no more than 10 ml of flushing fluid.

In certain embodiments, the system allows for relatively even rates of fluid flow through each of the two lumens. In some embodiments, the first and second lumens can be flushed without the need for a packaging mandrel.

Other features and advantages of the invention will be apparent from the description, drawings and claims.

DESCRIPTION OF DRAWINGS

FIG. 2E is a longitudinal cross-sectional view of the hub of FIGS. 2A-2D.

FIG. 2F is a transverse cross-sectional view of the hub of FIG. 2E, taken along line f-f.

FIG. 3A is a cross-sectional view of an embodiment of a hub.

Like reference symbols in the various drawings indicate like elements.

DETAILED DESCRIPTION

Figure 1:
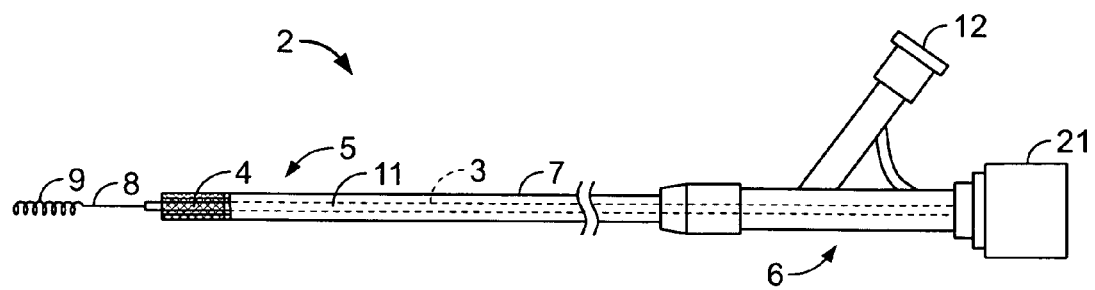
FIG. 1 is a partial cross-sectional side view of an embodiment of an implantable medical endoprosthesis delivery system.

FIG. 1 shows an implantable medical endoprosthesis delivery system 2 that is used to deliver and deploy an implantable medical endoprosthesis, in this case a stent 4. The implantable medical endoprosthesis delivery system 2 includes a first member 3 and a second member 7 surrounding first member 3. Stent 4 is positioned between the first member 3 and the second member 7. The implantable medical endoprosthesis delivery system 2 includes a distal end 5 dimensioned for insertion into a body lumen (e.g., an artery of a human) and a proximal end 6 that resides outside the body of a subject, and that optionally contains at least one port 12 and one or more lumens for manipulation by a physician. A guide wire 8 with a blunted end 9 is disposed in a lumen 11 contained within the first member 3. A hub 21, described in greater detail below, is disposed at the proximal end 6 of the system 2.

In some embodiments, the implantable medical endoprosthesis delivery system can be used to treat conditions within a body lumen, for example, an occluded artery, by bracing the lumen walls with, for example, a self-expanding stent. Generally, the blunted end of the guide wire is inserted into a body lumen by, for example, making an incision in the femoral artery, and directed to a constricted site of a lumen (e.g., an artery constricted with plaque) using, for example, fluoroscopy as a position aid. A proximal end of the guide wire remains outside of the body lumen throughout. After the guide wire has reached the constricted site the first and second members, with the stent disposed therebetween, are placed over the proximal end of the guide wire and moved distally over the guide wire until the stent is adjacent the constricted site of the body lumen. The second member is moved proximally, allowing the stent to expand and engage the lumen walls of the constricted site. The first and second members and the guide wire are removed from the body lumen, leaving the stent engaged with the lumen walls at the constricted site.

Figure 2A:
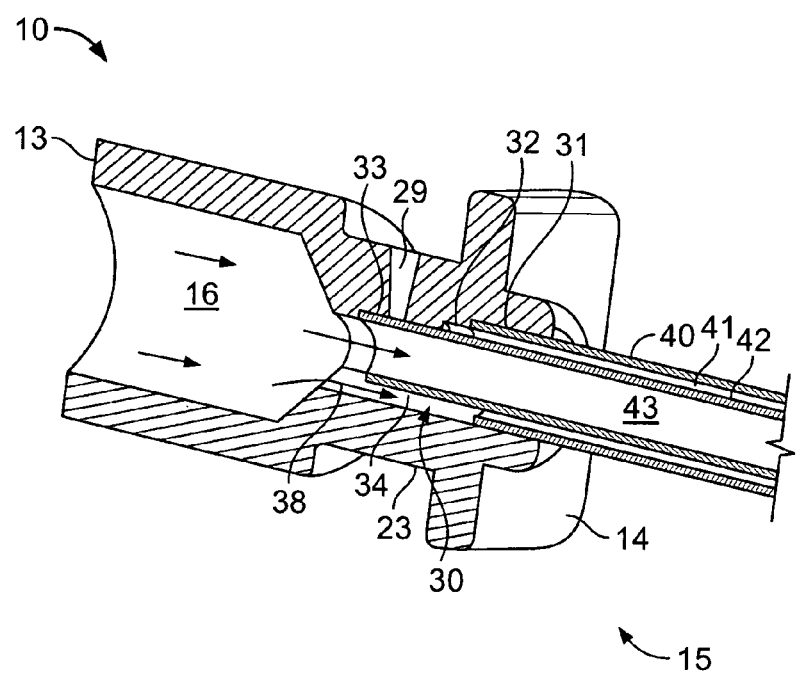
FIG. 2A is a perspective cross-sectional view of an implantable medical endoprosthesis delivery system.
Figure 2B:
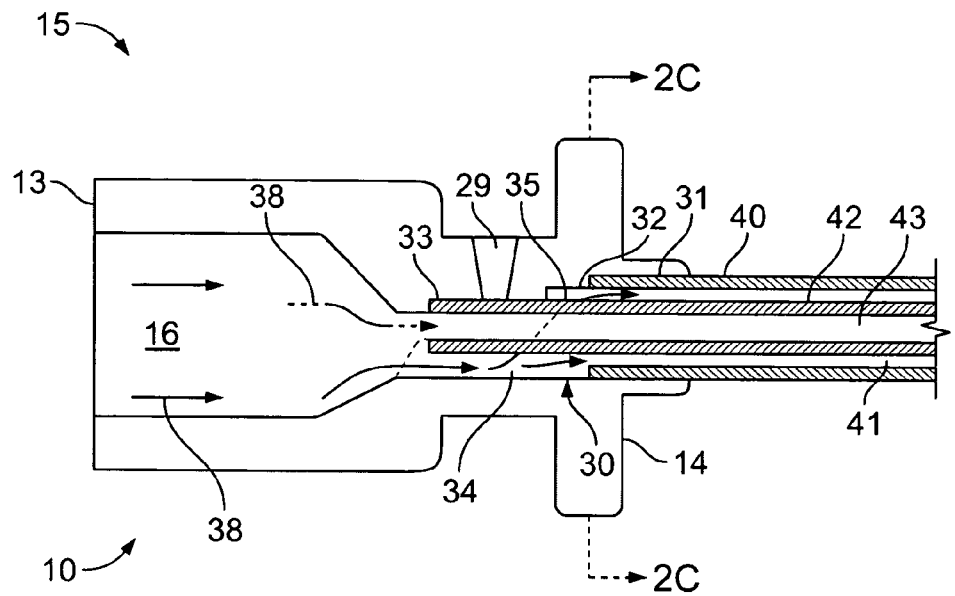
FIG. 2B is a longitudinal cross-sectional view of the implantable medical endoprosthesis delivery system of FIG. 2A.
Figure 2C:
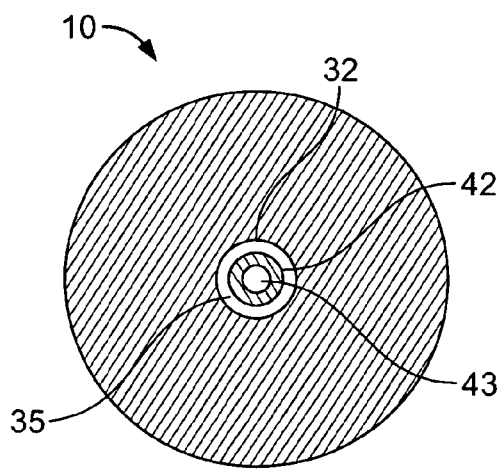
FIG. 2C is a transverse cross-sectional view of the implantable medical endoprosthesis delivery system of FIGS. 2A and 2B, taken along line c-c of FIG. 2B.
Figure 2D:
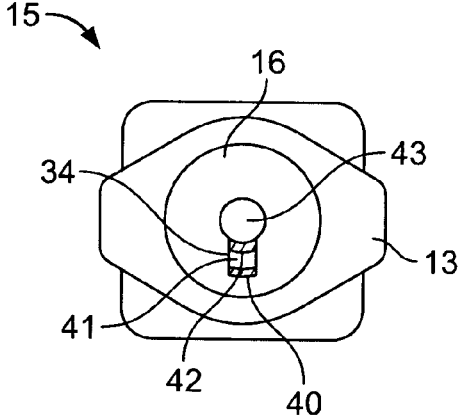
FIG. 2D is a view of the embodiment of FIGS. 2A-2C, taken from a proximal perspective.

FIGS. 2A-2D illustrate a first embodiment of an implantable medical endoprosthesis delivery system 15 including a hub 10, and FIGS. 2E-2F illustrate the hub 10 of system 15 absent the inner and outer members. Generally, the implantable medical endoprosthesis delivery system includes an inner member 42 having a first lumen 43 (e.g., a guide wire lumen) disposed therein and an outer member 40 that surrounds the inner member 42 such that there is a second lumen 41 disposed between the inner member 42 and the outer member 40. The hub 10 has a body 23 that includes a proximal recess 16 for receiving a fluid (e.g., a flushing fluid) and a longitudinal bore 30 in fluid communication with the proximal recess 16 and in fluid communication with the first and second lumens 43, 41 respectively. Fluid introduced into the proximal recess 16 can thus be directed into each of the first and second lumens 43, 41, simultaneously, allowing both lumens to be flushed at the same time. Such simultaneous flushing can allow the operator to reduce the number of steps in preparing the implantable medical endoprosthesis delivery system for use, which can ease the use and can shorten the time required to flush the device.

The hub 10 will now be described in greater detail. The hub 10 has a proximal end 13 and a distal end 14. The body 23 of the hub 10 includes a proximal recess 16 that is open to the proximal end 13. A longitudinal bore 30 extends from the distal end 14 and is in fluid communication with the proximal recess 16, such that the combined longitudinal bore 30 and proximal recess 16 form a lumen extending longitudinally through the body 23 of the hub I 0. Typically, the proximal recess 16 has a larger transverse diameter than does any part of the longitudinal bore 30, although in certain embodiments, part or all of the longitudinal bore 30 can have a larger transverse diameter than the proximal recess 16.

Figure 3B:
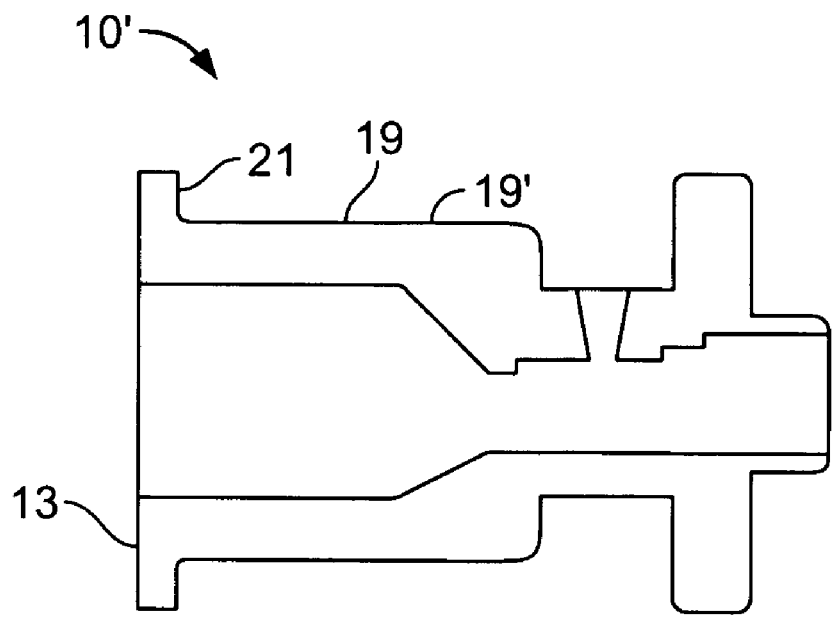
FIG. 3B is a cross-sectional view of an embodiment of a hub.
Figure 4:
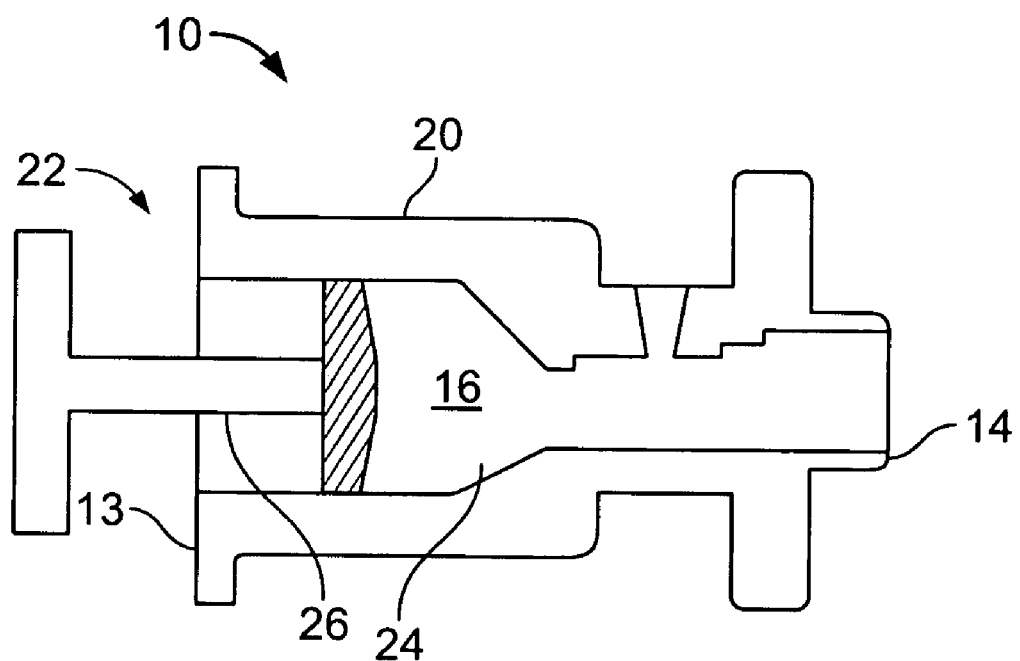
FIG. 4 is a cross-sectional view of an embodiment of a hub.

The proximal recess 16 is generally adapted for receiving a fluid introducer (not here illustrated) that is capable of introducing and imparting flow on a fluid (e.g., a flushing fluid) and optionally is capable of creating and optionally maintaining a pressure on the fluid. The fluid introducer can be, for example, a syringe, a hose, a pump, or any other suitable device. In some embodiments, the fluid introducer is held in the proximal recess 16 by the formation of an interference fit between the two. In other embodiments, for example, as illustrated in FIG. 3A, the fluid introducer is held in the proximal recess 16 via a thread 18 cut into an inner face 17 of a side wall 19 that forms a part of the proximal recess 16 and a corresponding thread on the fluid introducer (not illustrated). In another example, illustrated in FIG. 3B, the hub 10' includes luer threads 21 on an external side 19' of side wall 19, which can be operative to mate with a male luer on the fluid introducer. Other possible ways to connect the fluid introducer to the hub include snap-fittings, quick release fittings, or luer slip fittings. In some embodiments, the fluid introducer is connected to the hub in a permanent or semipermanent fashion, for example, by adhesive, welding (such as, e.g., chemical welding), or by forming part or all of the fluid introducer as a unitary or integral part of the hub. For example, in some embodiments, for example, as illustrated in FIG. 4, a barrel 20 of a syringe 22 is molded in a unitary fashion with the hub 10, such that an interior 24 of the syringe barrel forms the recess 16. A plunger 26 fits into the barrel 20 of the syringe 22. The plunger 26 is optionally removable for filling the barrel 20 with fluid.

Referring back to FIGS. 2E and 2F, the longitudinal bore 30 has a first, distal-most portion or segment 31 having a diameter a, a second portion 32 proximal to the first portion 31 and having a second diameter b, and a third portion 33 proximal to the second portion 32. The third portion 33 can be substantially circular and can have a diameter c extending across a circular portion of the segment. The third portion also has a transverse dimension d in a direction different from that of cross-section c, where dimension d is larger than dimension c. The dimension d arises as a result of a flush slot or channel 34 that extends longitudinally for the entire length of the third portion 33. Diameter a is sized to receive and secure a proximal end of an outer member 40 of an implantable medical endoprosthesis delivery system (shown in FIG. 2B), for example, by being adhered or otherwise connected to the outer member 40. Dimension c is sized to receive and secure a proximal end of an inner member 42 of an implantable medical endoprosthesis delivery system (shown in FIG. 2B), for example, by adhesive that is introduced into adhesive introduction hole 29 in body 23. The channel 34 in the third portion 33 extends the length of the third segment 33 from the recess 16 to the second portion 32. Diameter b is at least as large as an inner diameter of the outer member 40 and larger than the outer diameter of the inner member 42. As such, the second portion 32 of the bore 30 creates a counterbore flush slot 35 that extends between the inner member 42 and the outer member 40 and is in fluid contact with the channel 34, creating a fluid flow pathway from the recess 16 to lumen 41.

When fluid is introduced into the recess 16 (e.g., via a syringe attached to the hub 10 at the proximal end 13 of the hub) fluid will flow (indicated by arrows 38) into both the lumen 43 in the inner member 42 and, via the channel 34 extending the length of the third portion 33, into the second portion 32. Once in the second segment 32, the fluid can flow into the lumen 41 between the inner member 42 and the outer member 40.

Figure 5A:
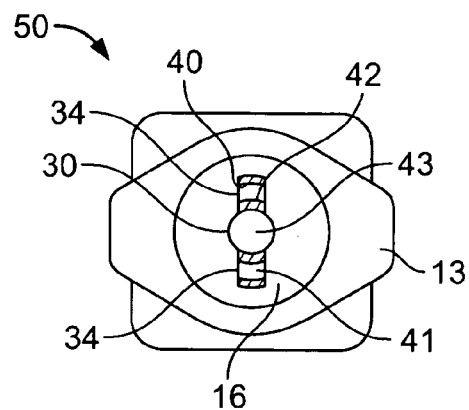
FIGS. 5A-5C are views of embodiments of a hub taken from a proximal perspective.
Figure 5B:
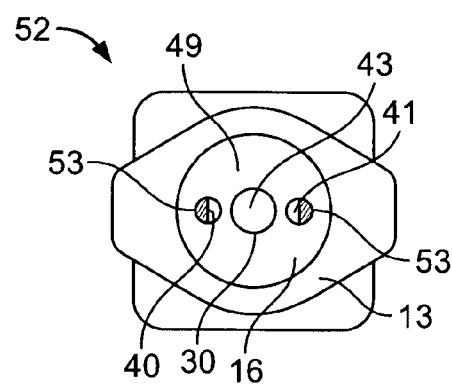
Figure 5C:
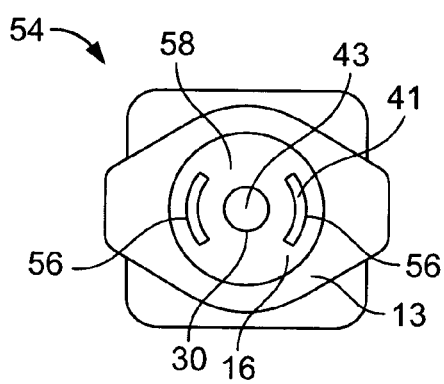

While the embodiment illustrated above employ a single flush slot, in other embodiments, multiple flush slots can be employed, which can provide for greater volumes of fluid flow into the lumen between the inner and outer members. For example, in FIG. 5A, a hub 50 includes two flush slots or channels 34, each connected to the proximal part of the bore 30. In a hub embodiment 52 of FIG. 5B, the channel is replaced by a pair of flush ports 53, which extend from the recess 16 to a proximal end of the lumen 41 between the inner member 42 (which here resides behind the distal wall 49 of the recess 16) and outer member 40. In an embodiment illustrated in FIG. 5C, a hub 54 includes a pair of arc-shaped flush ports 56, which extend from the recess 16 to a proximal end of the lumen 41 between the inner member 42 and outer member 40, each of which here resides behind the distal wall 58 of the recess 16.

Figure 6:
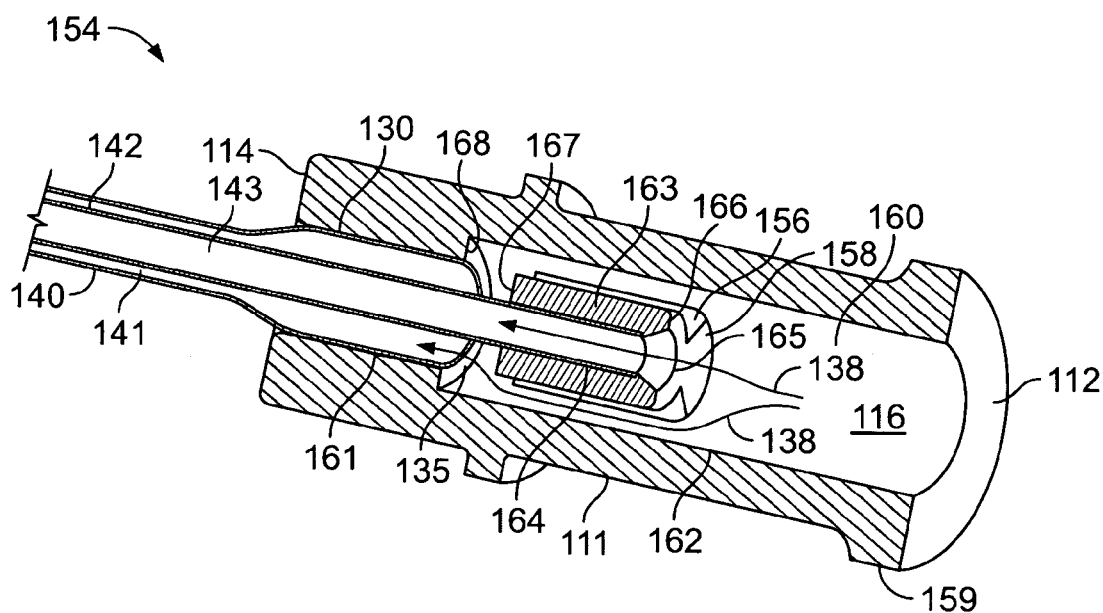
FIG. 6 is an embodiment of a hub shown in a perspective cross-sectional view.

Another embodiment is illustrated in FIG. 6, in which a hub 154 has a longitudinal bore 160 extending from a proximal end 112 to a distal end 114. The longitudinal bore 160 includes a first segment 161 having a first diameter and a second segment 162 disposed proximally of the first segment and having a second diameter that is no smaller than the first diameter. A tubular inner collar 163 is disposed within the second segment. The inner collar 163 has an inner collar bore 164 having a diameter smaller than the first diameter. The outer member 140 extends into and is attached to the first segment 161 of the longitudinal bore 160. The inner member 142, concentrically disposed within the outer member 140, extends into the longitudinal bore 160 and into the inner collar bore 164, where it is secured.

The inner collar 163 has a proximal end 166 that is distal the proximal end 112 of the hub, and a recess 116 extends proximally from the inner collar 163 to the proximal end 112 of the hub. The inner collar 163 further has a distal end 167 that is proximal to a distal end 168 of the second segment 162, with a counterbore flush slot 135 disposed between the two. The inner collar is connected to the hub body by a pair of connectors 165 (only one is illustrated) that do not extend around the full circumference of the inner collar 163. The portions of the inner collar around which the connectors do not extend form a pair of flush ports 156 that extend from, and put into fluid communication, the recess 116 and the counterbore flush slot 135. The counterbore flush slot 135 permits fluid flowing distally through the flush ports 156 to completely encircle the inner member 142 and thus completely fill (and flush) the lumen 141 that lies between the inner and outer members 142, 140. Fluid flow, indicated by arrows 138, will be directed to both the inner tube lumen 143 and the lumen 141 between the inner and outer tubes 142, 140.

The inner catheter and/or outer members can be made of, for example, one or more polymers. Examples of polymers include polyether-block co-polyamide polymers (e.g., PEBAX®), copolyester elastomers (e.g., Amitel® copolyester elastomers), thermoset polymers, polyolefins (e.g., Marlex® polyethylene, Marlex® polypropylene), high-density polyethylene (HDPE), low-density polyethylene (LDPE), polyamides (e.g., Vestamid®), polyetheretherketones (PEEKs), and silicones. Other examples of polymers include thermoplastic polymers, such as polyamides (e.g., nylon), thermoplastic polyester elastomers (e.g., Hytrel®), and thermoplastic polyurethane elastomers (e.g., Pellethane™). The inner member and the outer member can include the same polymers and/or can include different polymers.

The lumen located within the inner member can have an inner diameter of any size suitable for use as a part of a catheter system. In some embodiments, the lumen located within the inner member can have an inner diameter of at least about 0.05 cm (e.g., at least about 0.06 cm, at least about 0.07 cm, at least about 0.08 cm, at least about 0.09 cm, at least about 0.10 cm, at least about 0.11 cm, or at least about 0.12 cm) and/or at most about 0.13 cm (e.g., at most about 0.12 cm, at most about 0.11 cm, at most about 0.1 cm, at most about 0.09 cm, at most about 0.08 cm, at most about 0.07 cm, or at most about 0.06 cm). The inner member can have an outer diameter of at least about 0.07 cm (e.g., at least about 0.08 cm, at least about 0.09 cm, at least about 0.1 cm, at least about 0.11 cm, at least about 0.12 cm, at least about 0.13 cm, at least about 0.14 cm, at least about 0.15 cm, or at least about 0.17 cm) and/or at most about 0.18 cm (e.g., at most about 0.17 cm, at most about 0.16 cm, at most about 0.15 cm, at most about 0.14 cm, at most about 0.13 cm, at most about 0.12 cm, at most about 0.11 cm, at most about 0.1 cm, at most about 0.09 cm, or at most about 0.08 cm). The inner lumen may have a transverse cross-sectional area of at least about 0.6 mm$^2$ (e.g., at least about 1 mm$^2$, at least about 2 mm$^2$, at least about 3 mm$^2$, at least about 4 mm$^2$, or at least about 5 mm$^2$) and/or at most about 5.5 mm$^2$ (e.g., at most about 5 mm$^2$, at most about 4 mm$^2$, at most about 3 mm$^2$, at most about 2 mm$^2$, or at most about 1 mm$^2$). The lumen located within the inner member may be a guide wire lumen. In some embodiments, the guide wire lumen can be coated with a polymer (e.g., a polyimide) that can decrease friction between the guide wire lumen and a guide wire that is disposed within guide wire lumen.

The outer member can have an inner diameter of any size suitable for use as a part of a catheter system, for example, of sufficient size to receive the inner member and permit flushing of the outer lumen. In some embodiments, the outer member can have an inner lumen having an inner diameter of at least about 0.08 cm (e.g., at least about 0.1 cm, at least about 0.12 cm, at least about 0.14 cm, at least about 0.16 cm, or at least about 0.18 cm) and/or at most about 0.2 cm (e.g., at most about 0.18 cm, at most about 0.16 cm, at most about 0.14 cm, at most about 0.12 cm, or at most about 0.1 cm). The outer member can have an outer diameter of at least about 0.10 cm (e.g., at least about 0.12 cm, at least about 0.14 cm, at least about 0.16 cm, at least about 0.18 cm, at least about 0.20 cm, or at least about 0.22 cm) and/or at most about 0.24 cm (e.g., at most about 0.22 cm, at most about 0.20 cm, at most about 0.18 cm, at most about 0.16 cm, at most about 0.14 cm, or at most about 0.12 cm). The second lumen (e.g., the lumen between the inner and outer members) may have a transverse cross-sectional area of at least about 0.6 mm$^2$ (e.g., at least about 1 mm$^2$, at least about 2 mm$^2$, at least about 4 mm$^2$, at least about 6 mm$^2$, at least about 8 mm$^2$, or at least about 10 mm$^2$) and/or at most about 12 mm$^2$ (e.g., at most about 10 mm$^2$, at most about 8 mm$^2$, at most about 6 mm$^2$, at most about 4 mm$^2$, at most about 2 mm$^2$, or at most about 1 mm$^2$).

In certain embodiments, the outer member is a tube (e.g., a hypotube). The hypotube is in some embodiments formed of a metal or alloy (e.g., stainless steel). The hypotube in some embodiments includes a sheath disposed on the outer surface of the hypotube. Typically, such a sheath is formed of a polymer, such as a thermoplastic elastomer (e.g., a heat shrinkable polymer). Examples of polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters (e.g., polyetheretherketones (PEEKs), polyurethanes, polyethylenes, polypropylenes, copolymers and ionomers of ethylene, copolymers and ionomers of polypropylene, polystyrenes and copolymers of polystyrenes. Examples of commercially available polyesters include the Selar® PT family of polymers (e.g., Selar® PT 8307, Selar® PT4274, Selar® PTX280), which are commercially available from E. I. DuPont de Nemours (Wilmington, Del.), the Cleartuf® family of polymers (e.g., Cleartuf® 8006), which are commercially available from M&G Polymers (Apple Grove, W. Va.), the Traytuf® family of polymers (e.g., Traytuf® 1006), which are commercially available from the Shell Chemical (Houston, Tex.), the Melinar® family of polymers, commercially available from E. I. DuPont de Nemours (Wilmington, Del.), the Celanex® family of polymers, commercially available from Ticona (Summit, N.J.), the Riteflex® family of polymers, commercially available from Ticona (Summit, N.J.), the Hytrel® family of polymers (e.g., Hytrel® 5556, Hytrel® 7246, Hytrel® 4056), commercially available from E. I. DuPont de Nemours (Wilmington, Del.), the Arnitel® family of polymers (e.g., Amitel® EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid® family of polymers (e.g., Grilamid® L25, Grilamid® L20), commercially available from EMS (Sumter, S.C.), the Vestamid® family of polymers (e.g., Vestamid® L2101F), commercially available from Daicel-Degussa Ltd., and the PEBAX® family of polymers (e.g., PEBAX® 5533, PEBAX® 2533, PEBAX® 7033), commercially available from Atofina (Philadelphia, Pa.), the Trogamid® family of polyamides from Daicel-Degussa, Cristamid® MS 1100 from Atofina (Philadelphia, Pa.), and Vestamid® L2101 F nylon 12 from Degussa AG An example of a commercially available polyethylene is Marlex 4903 high density polyethylene from Phillips 66 (Bartlesville, Okla.). Hypotubes and hypotube sheaths are described in U.S. patent application Ser. No. 10/256,612, titled "SHEATH MATERIALS AND PROCESSES", and filed on Sep. 26, 2002, the entire contents of which are hereby incorporated by reference.

In certain embodiments, the inner and/or outer members extend substantially the entire length of the implantable medical endoprosthesis delivery system. In other embodiments, one or both of the inner and outer members are connected to adjacent inner 20 and/or outer members such that the first and second lumens extend substantially the entire length of the catheter delivery system. In some embodiments, the first and/or second lumens are at least about 40 cm long (e.g., at least about 50 cm, at least about 75 cm, at least about 100 cm, at least about 125 cm, at least about 150 cm, at least about 175 cm, at least about 200 cm, or at least about 225 cm long) and/or at most about 250 cm long (e.g., at most about 225 cm, at most about 200 cm, at most about 175 cm, at most about 150 cm, at most about 125 cm, at most about 100 cm, at most about 75 cm, or at most about 50 cm long). In some embodiments, the volume of fluid required to flush the lumens, in total, is no more than about 25 ml (e.g., no more than about 15 ml, 10 ml, 9 ml, 8 ml, 7 ml, 6 ml, or 5 ml) and/or no less than about 4 ml (e.g., no less than about 5 ml, 6 ml, 7 ml, 8 ml, 9 ml, 10 ml, 15 ml, or 25 ml). For example, in some embodiments, a 10-ml syringe having no more than 10 ml of fluid is sufficient to flush both lumens simultaneously.

In some embodiments, one or more regions of the inner member and/or the outer member can be formed by an extrusion process. In some embodiments, different regions (e.g., different regions made up of different polymers) can be integrally formed. In certain embodiments, different regions can be separately formed and then connected together.

In certain embodiments, the inner catheter and/or the outer catheter can be formed of multiple layers. For example, the outer catheter can include three layers: an outer polymer layer, an inner polymer layer, and an intermediate structural layer disposed between the inner and outer layers. The inner polymer layer can be, for example, polytetrafluoroethylene (PTFE), such as PTFE that has been etched on a surface that is to be bonded to the middle layer (e.g., to improve bonding to other layers). The intermediate structural layer can be, for example, a braid layer. In certain embodiments, the braid layer can be formed of a metal (e.g., tungsten) or metal alloy (e.g., stainless steel). In some embodiments, the braid layer can include one or more flat wires and/or one or more round wires. In certain embodiments, the braid layer can form a pattern between the inner layer and the outer layer. The outer polymer layer can be, for example, nylon, PEBAX®, Amitel®, or Hytrel®.

In some embodiments, the inner catheter and/or outer catheter can be formed of multiple polymer layers of differing durometers. In certain embodiments, the inner catheter and/or the outer catheter can include multiple coextruded layers. For example, an inner catheter with an inner layer including HDPE, an outer layer including PEBAX®, and a tie layer between the inner and outer layers can be formed by coextrusion.

Coextrusion processes are described in, for example, U.S. Patent Application Publication No. US 2002/0165523 A1, published on Nov. 7, 2002, and U.S. patent application Ser. No. 10/351,695, filed on Jan. 27, 2003, and entitled "Multi-layer Balloon Catheter", both of which are incorporated herein by reference.

Generally, the flow path from the recess to the lumen between the inner and outer members (the second lumen) is less direct (e.g., requires fluid to flow in a non-linear fashion). Also, generally, the cross-sectional surface area of the second lumen and/or the flush slot or port connecting the recess to the second lumen is smaller than that of the first lumen. Given this, fluid introduced into the hub may in some embodiments tend to flow along a path of least resistance (e.g., into the first, inner tube lumen) to the at least partial exclusion of the second lumen. This can in some embodiments be corrected by partially obstructing the flow of fluid into the first lumen, thus directing more into the second lumen. The result is a high volume of flushing fluid being required to adequately flush both lumens (e.g., 25 ml or more of flushing fluid). A larger syringe (e.g., a 25 cc syringe) can be used to accommodate this volume of fluid; however, typically, smaller syringes provide greater fluid pressure than do larger syringes. For this reason, in certain embodiments, it may be preferable to use smaller syringes (e.g., a 10 cc syringe or a 5 cc syringe).

Figure 7:
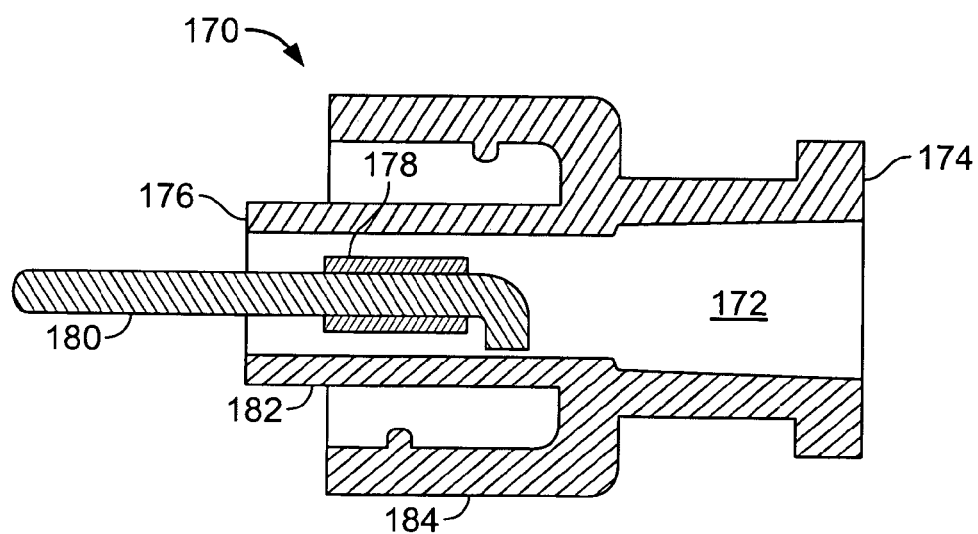
FIG. 7 is a cross-sectional view of an embodiment of a flow restrictor.
Figure 8:
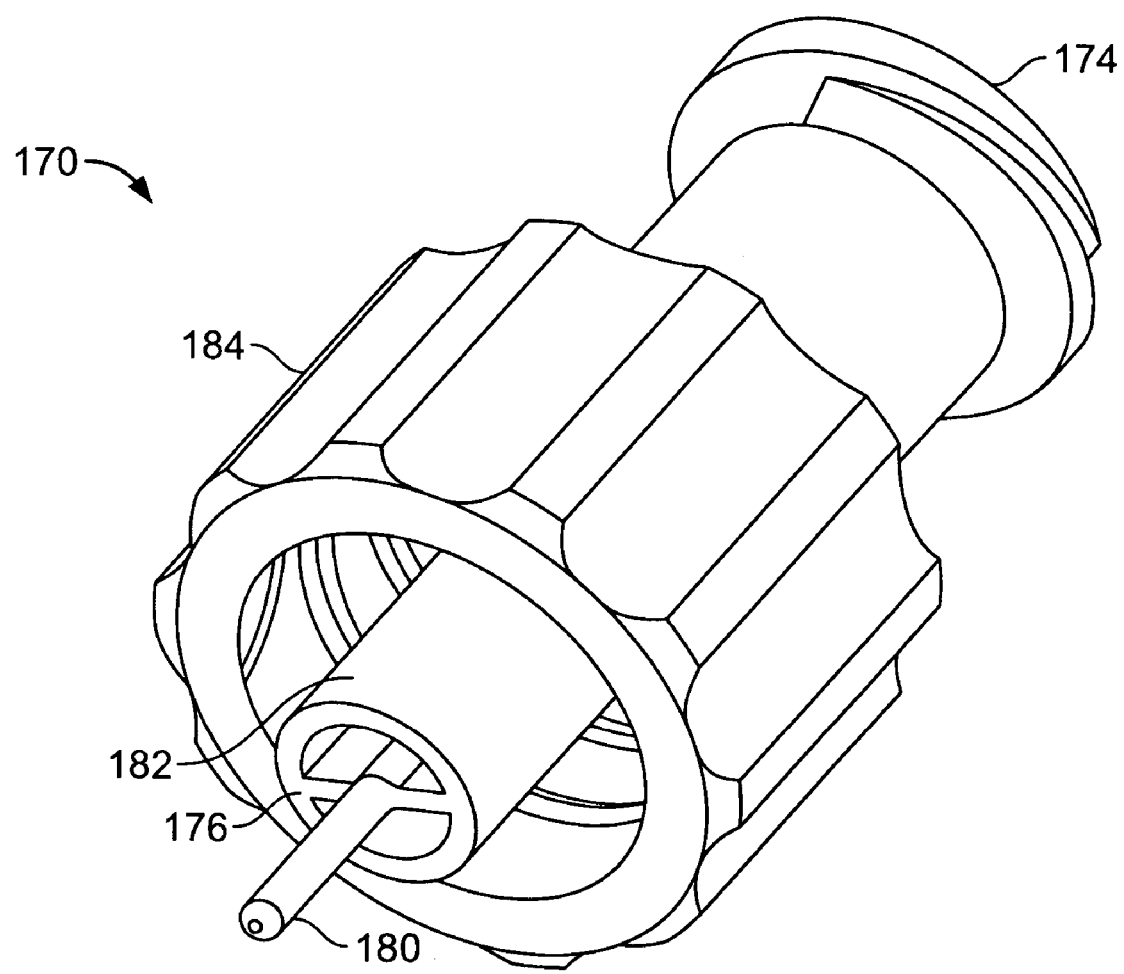
FIG. 8 is a perspective view of the embodiment of FIG. 7.
Figure 9:
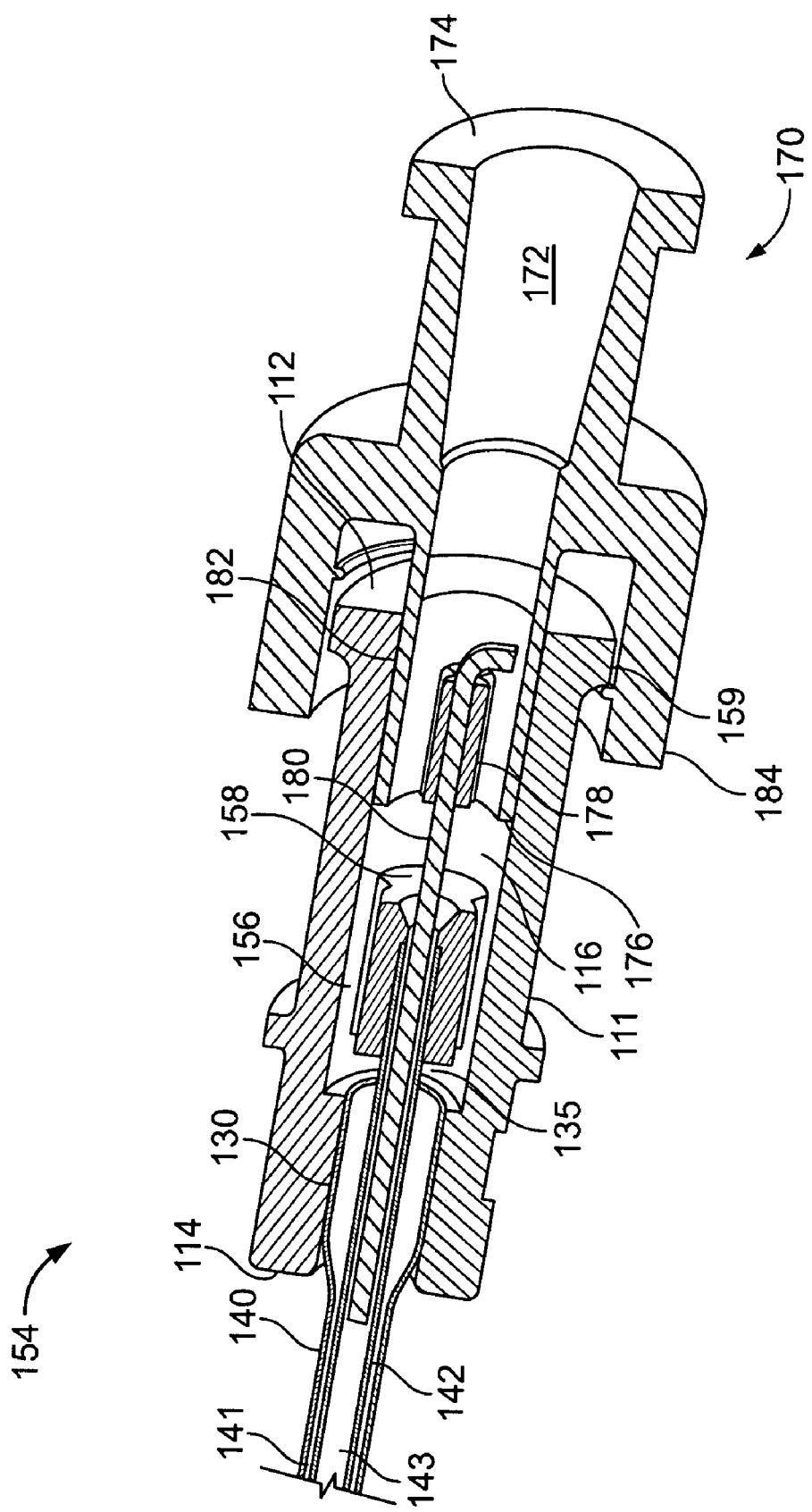
FIG. 9 is an embodiment of a hub shown in a perspective cross-sectional view.

A flow restrictor, an embodiment of which is illustrated in FIGS. 7 and 8, can be employed to permit flushing of both lumens using lower volumes of flushing fluid. The flow restrictor 170 includes a central flow chamber 172 through which fluid can flow from a proximal end 174 of the flow restrictor to a distal end 176 of the flow restrictor. Disposed within the central bore is a mounting member 178 in which is mounted an flow restrictor 180. In use, as illustrated in FIG. 9, the flow restrictor 170 is inserted into the proximal end 112 of the hub 154 such that a distal portion 182 of the flow restrictor 170 resides within the recess 116 of the hub 154. The flow restrictor 170 is attached to the hub 154 in this position via a female luer 184 on the flow restrictor that interacts with a male luer 159 on the hub 154. The flow restrictor 180 is in this case in the form of a solid cylindrical tube that extends into the first lumen 143. The flow restrictor tube 180 has a diameter less than that of the first lumen 143 to partially but not fully restrict the flow of fluid into the first lumen 143. For example, the flow restrictor tube in some embodiments has a diameter of no more than about 0.12 cm (e.g., no more than about 0.10 cm, no more than about 0.08 cm, no more than about 0.06 cm, or no more than about 0.04 cm) and/or no less than about 0.02 cm (e.g., no less than about 0.04 cm, no less than about 0.06 cm, no less than about 0.08 cm, or no less than about 0.10 cm). Generally, the flow restrictor can be any shape and dimension that permits partial occlusion of the first lumen, generally by reducing the available transverse cross-sectional area of the first lumen that is available for fluid flow therethrough (e.g., by occluding the entrance to the first lumen or by extending into and partially occluding the first lumen). In some embodiments, the insertion of the flow restrictor into the first lumen reduces the transverse cross-sectional area of the lumen at its proximal end by at least about 25% (e.g., at least about 40%, at least about 50%, at least about 60%, at least about 70%, at least about 80% or at least about 90%) and/or at most about 95% (e.g., at most about 90%, at most about 80%, at most about 70%, at most about 60%, at most about 50%, or at most about 40%). In some embodiments, the transverse cross-sectional areas of the first and second lumens at their proximal ends with the flow restrictor in position, differ by no more than about 50% (e.g., no more than about 40%, no more than about 30%, no more than about 25%, no more than about 20%, no more than about 15%, no more than about 10% or no more than about 5%).

In certain embodiments, the throughput of fluid through the first lumen is no more than about 80% different (e.g., is no more than about 60% different, no more than about 40% different, or no more than about 20% different) than the throughput of fluid through the second lumen when the flow restrictor is used.

The flow restrictor 170 is mounted onto the proximal end 112 of the hub 154, as illustrated in FIG. 9, and a syringe (not illustrated) is attached to the flow restrictor. The pin 180 of the flow restrictor 170 extends into the first lumen 143, reducing the area into which fluid can flow. Once the first and second lumens 143, 141, have been flushed, the flow restrictor is removed from the hub, clearing the proximal end of the first lumen for acceptance of a guide wire.

While certain embodiments have been disclosed, other embodiments are possible. For example, while the inner and outer members (and corresponding components of the hub and associated components) are shown in the figures as being tubular and having substantially circular cross-sections, the inner and outer members can have other cross-sectional configurations (e.g., elliptical or polygonal). The inner and outer members further need not have the same cross-sectional configuration (e.g., the inner can be polygonal while the outer is circular).

As another example, while the hubs herein have been shown in conjunction with a dual-tube implantable medical endoprosthesis delivery system, the concept can be utilized for more than two tubes or lumens (e.g., three four, five or more tubes). Further, while the tubes shown here are concentric, one or more of the tubes need not be concentric.

As yet another example, while embodiments having one or two flush slots or flush ports have been illustrated, the number of flush slots or flush ports can vary; for example, embodiments can include three or more (e.g., four or more, five or more, six or more, seven or more) flush ports or slots. The ports or slots can have any shape (e.g., circular, arcuate, ovoid, polygonal).

As still another example, while embodiments presented have included a counterbore flush slot that is disposed just proximal the proximal end of the outer tube and which permits fluid to flow around the inner member to completely encircle the inner member (and thus completely flush the lumen between the inner member and the outer member), in certain embodiments the flush slot(s) or flush port(s) extend from the recess to the lumen between the inner and outer members (i.e. there is no counterbore flush slot). Fluid can flow into the lumen between the inner and outer members and there encircle the inner member to permit complete flushing of the lumen.

As a further example, embodiments can have multiple adhesive holes that permit the adhering of the inner and/or outer members to the hub.

As yet another example, while flow restrictors utilizing pins have been described, other devices that restrict the flow of fluid could be employed. For example, a Tuohy-Borst can be employed in which a gasket having an infinite through-hole partially obstructs the flow of fluid into the first lumen. The diameter of the through-hole can be adjusted by tightening or loosening the gasket, allowing for adjustment of the degree of obstruction of the flow of fluid into the first lumen. In other embodiments, a guide wire could be used to obstruct the flow of fluid into the first lumen.

As another example, in some embodiments, the outer member is a hypotube (e.g., a stainless steel tube, optionally coated at least in part by a coating, for example, a polymeric coating). In other embodiments, the outer member is a polymeric tube (e.g., a catheter tube) and can be formed in accordance with any known catheter tube.

As still another example, the implantable medical endoprosthesis delivery system can be configured to deliver an implantable medical endoprosthesis, for example, a stent, a stent-graft, or a graft. The endoprosthesis can be a self-expanding endoprosthesis, a balloon-expandable endoprosthesis, or a combination thereof.

Other embodiments are within the scope of the following claims.

What is claimed is:

1. An implantable medical endoprosthesis delivery system, comprising:
    an inner member having a first lumen disposed therein;
    an outer member at least partially surrounding the inner member so that a second lumen is disposed between the inner and outer members, the second lumen being configured so that an implantable medical endoprosthesis can be disposed therein;
    a hub including a fluid introduction port, a first fluid flow path in fluid communication with the fluid introduction port, and a second fluid flow path in fluid communication with the fluid introduction port;
    wherein the first flow path is in fluid communication with the first lumen and the second flow path is in fluid communication with the second lumen;
    wherein the hub comprises a body having a proximal face, a distal face, and a bore extending from the proximal face through the body to the distal face, the bore being in fluid communication with the first and second lumens
    wherein the body comprises:
        a first section that defines a first portion of the bore; and
        a second section proximal the first section, the second section defining a second portion of the bore;
        wherein the first portion of the bore receives a proximal end of the outer member, the second portion of the bore receives a proximal end of the inner member, and the second portion of the bore includes a channel that defines at least a portion of the second fluid flow path; and
    wherein the first portion of the bore has a diameter larger than a diameter of the second portion of the bore.

2. The delivery system of claim 1, wherein the first lumen is configured to receive a guide wire.

3. The delivery system of claim 1, wherein the outer member comprises a hypotube.

4. The delivery system of claim 3, wherein the outer member further comprises a polymeric tube connected to the hypotube.

5. The delivery system of claim 1, further comprising a fluid introduction device configured to introduce fluid into the fluid introduction port.

6. The delivery system of claim 5, wherein the fluid introduction port comprises a recess for receiving the fluid introduction device.

7. The delivery system of claim 1, wherein the body further comprises a third section proximal the second section, the third section defining a third portion of the bore, and the third portion of the bore being in fluid communication with the channel and with the fluid introduction port.

8. The delivery system of claim 1, wherein a proximal end of the outer member is affixed to the hub, and a proximal end of the inner member is affixed to the hub, the proximal end of the inner member being proximal to the proximal end of the outer member.

9. The delivery system of claim 1, further comprising a flow restrictor configured to partially occlude a proximal end of the first lumen.

10. The delivery system of claim 9, wherein the flow restrictor is removable from the system.

11. The delivery system of claim 9, wherein the flow restrictor comprises a pin that is inserted into the proximal end of the first lumen.

12. The delivery system of claim 9, wherein the hub comprises a male luer or a female luer, and the flow restrictor comprises the other of a male luer or a female luer.

13. The delivery system of claim 9, wherein the flow restrictor is configured to allow fluid to flow longitudinally therethrough.

14. The delivery system of claim 9, wherein, during use, the throughput of fluid through the first lumen is no more than about 80% different than the throughput of fluid through the second lumen.

15. The delivery system of claim 9, wherein, during use, the throughput of fluid through the first lumen is no more than about 60% different than the throughput of fluid through the second lumen.

16. The delivery system of claim 9, wherein, during use, the throughput of fluid through the first lumen is no more than about 40% different than the throughput of fluid through the second lumen.

17. The delivery system of claim 9, wherein, during use, the throughput of fluid through the first lumen is no more than about 20% different than the throughput of fluid through the second lumen.

18. The delivery system of claim 9, wherein the flow restrictor comprises a pin that extends into the proximal end of the first lumen, the proximal end of the first lumen has a transverse cross-sectional area, and the pin has a transverse cross-sectional area that is at least about 90% of the transverse cross-sectional area of the proximal end of the first lumen.

19. An implantable medical endoprosthesis delivery system, comprising:
    an inner member having a first lumen disposed therein;
    an outer member at least partially surrounding the inner member so that a second lumen is disposed between the inner and outer members, the second lumen being configured so that an implantable medical endoprosthesis can be disposed therein;
    a hub including a fluid introduction port, a first fluid flow path in fluid communication with the fluid introduction port, and a second fluid flow path in fluid communication with the fluid introduction port,
    wherein the first flow path is in fluid communication with the first lumen and the second flow path is in fluid communication with the second lumen;
    wherein the hub comprises a body having a proximal face, a distal face, and a bore extending from the proximal face through the body to the distal face, the bore being in fluid communication with the first and second lumens;
    wherein the body comprises:
        a first section that defines a first portion of the bore; and
        a second section proximal the first section, the second section defining a second portion of the bore;
        wherein the first portion of the bore receives a proximal end of the outer member, the second portion of the bore receives a proximal end of the inner member, and the second portion of the bore includes a channel that defines at least a portion of the second fluid flow path;
    wherein the body further comprises a third section proximal the second section, the third section defining a third portion of the bore, and the third portion of the bore being in fluid communication with the channel and with the fluid introduction port; and
    wherein the third portion of the bore has a diameter smaller than a diameter of the second portion of the bore.

20. An implantable medical endoprosthesis delivery system, comprising:
    an inner member having a first lumen disposed therein;
    an outer member at least partially surrounding the inner member so that a second lumen is disposed between the inner and outer members, the second lumen being configured so that an implantable medical endoprosthesis can be disposed therein;
    a hub including a fluid introduction port, a first fluid flow path in fluid communication with the fluid introduction port, and a second fluid flow path in fluid communication with the fluid introduction port,
    wherein the first flow path is in fluid communication with the first lumen and the second flow path is in fluid communication with the second lumem;
    wherein the hub comprises a body having a proximal face, a distal face, and a bore extending from the proximal face through the body to the distal face, the bore being in fluid communication with the first and second lumens;
    wherein the body comprises:
        a first section that defines a first portion of the bore; and
        a second section proximal the first section, the second section defining a second portion of the bore;
        wherein the first portion of the bore receives a proximal end of the outer member, the second portion of the bore receives a proximal end of the inner member, and the second portion of the bore includes a channel that defines at least a portion of the second fluid flow path;
    wherein the body further comprises a third section proximal the second section, the third section defining a third portion of the bore, and the third portion of the bore being in fluid communication with the channel and with the fluid introduction port; and
    wherein the body further comprises a fourth section disposed between the first and second sections and defining a counterbore flush slot that extends circumferentially around the inner member and is in fluid communication with the channel and the second lumen.

* * * * *

UNITED STATES PATENT AND TRADEMARK OFFICE
CERTIFICATE OF CORRECTION

PATENT NO. : 7,621,946 B2
APPLICATION NO. : 11/368876
DATED : November 24, 2009
INVENTOR(S) : Karen Turner et al.

It is certified that error appears in the above-identified patent and that said Letters Patent is hereby corrected as shown below:

Column 12
Line 33, after "second", delete "lumem", and insert therefor -- lumen --.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,621,946 B2  Page 1 of 1
APPLICATION NO. : 11/368876
DATED : November 24, 2009
INVENTOR(S) : Turner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 912 days.

Signed and Sealed this

Twenty-sixth Day of October, 2010

David J. Kappos
*Director of the United States Patent and Trademark Office*